(12) United States Patent
Salnik et al.

(10) Patent No.: US 7,982,867 B2
(45) Date of Patent: Jul. 19, 2011

(54) METHODS FOR DEPTH PROFILING IN SEMICONDUCTORS USING MODULATED OPTICAL REFLECTANCE TECHNOLOGY

(75) Inventors: Alex Salnik, Castro Valley, CA (US); Jon Opsal, Livermore, CA (US); Lena Nicolaides, Castro Valley, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 12/767,339

(22) Filed: Apr. 26, 2010

(65) Prior Publication Data

US 2010/0315625 A1    Dec. 16, 2010

Related U.S. Application Data

(63) Continuation of application No. 11/998,118, filed on Nov. 28, 2007, now Pat. No. 7,705,977.

(60) Provisional application No. 60/876,247, filed on Dec. 21, 2006.

(51) Int. Cl.
*G01N 21/00* (2006.01)
(52) U.S. Cl. .................... 356/237.2; 356/237.3
(58) Field of Classification Search ..... 356/237.1–237.5
See application file for complete search history.

(56) References Cited

U.S. PATENT DOCUMENTS

| | | |
|---|---|---|
| 4,634,290 A | 1/1987 | Rosencwaig et al. |
| 4,646,088 A | 2/1987 | Inoue |
| 5,074,669 A | 12/1991 | Opsal |
| 5,854,710 A | 12/1998 | Rao et al. |
| 5,978,074 A | 11/1999 | Opsal et al. |
| 6,191,846 B1 | 2/2001 | Opsal et al. |
| 6,320,666 B1 | 11/2001 | Opsal et al. |
| 6,453,685 B2 | 9/2002 | Ota et al. |
| 6,522,413 B2 | 2/2003 | Opsal et al. |
| 6,678,046 B2 | 1/2004 | Opsal |
| 6,813,034 B2 | 11/2004 | Rosencwaig et al. |
| 6,836,338 B2 | 12/2004 | Opsal et al. |
| 7,079,249 B2 | 7/2006 | Nicolaides et al. |
| 7,248,367 B2 | 7/2007 | Salnik et al. |
| 7,280,215 B2 | 10/2007 | Salnik et al. |
| 7,499,168 B2 | 3/2009 | Salnik et al. |
| 7,502,104 B2 | 3/2009 | Salnik et al. |
| 2006/0166385 A1 | 7/2006 | Salnik et al. |
| 2008/0074668 A1 | 3/2008 | Salnik et al. |

OTHER PUBLICATIONS

T. Clarysse et al., "Carrier Illumination for Characterization of Ultra-Shallow Doping Profiles," *Book of Abstracts, 7th Int. Workshop on: Fabrication, Characterization, and Modeling of USJ Doping Profiles in Semiconductors (USJ-2003)*, Santa Cruz, CA, Apr. 27-May 1, 2003, pp. 321-327.

(Continued)

*Primary Examiner* — Michael P Stafira
(74) *Attorney, Agent, or Firm* — Morrison & Foerster LLP

(57) ABSTRACT

Methods of obtaining dopant and damage depth profile information are disclosed using modulated optical reflectivity (MOR) measurements. In one aspect, the depth profile is constructed using information obtained from various measurements such as the junction depth, junction abruptness and dopant concentration. In another aspect, a full theoretical model is developed. Actual measurements are fed to the model. Using an iterative approach, the actual measurements are compared to theoretical measurements calculated from the model to determine the actual depth profile.

16 Claims, 14 Drawing Sheets

OTHER PUBLICATIONS

T. Clarysse et al., "Towards nondestructive carrier depth profiling," *J. Vac. Sci. Technol. B*, vol. 24, No. 3, May/Jun. 2006, pp. 1139-1146.

A. Mandelis et al., "Generalized methodology for thermal diffusivity depth profile reconstruction in semi-infinite and finitely thick inhomogeneous solids," *J. Appl. Phys.*, vol. 80, No. 10, Nov. 15, 1996, pp. 5570-5578.

A. Salnick et al., "Quantitative Photothermal characterization of ion-implanted layers in Si," *Journal of Applied Physics*, vol. 91, No. 5, Mar. 1, 2002, pp. 2874-2882.

A. Salnick et al., "Hamiltonian plasma-harmonic oscillator theory: Generalized depth profilometry of electronically continuously inhomogeneous semiconductors and the inverse problem," *J. Appl. Phys.*, vol. 80, No. 9, Nov. 1, 1996, pp. 5278-5288.

METHODS FOR DEPTH PROFILING IN SEMICONDUCTORS USING MODULATED OPTICAL REFLECTANCE TECHNOLOGY

PRIORITY

This application is a continuation of U.S. patent application Ser. No. 11/998,118, filed Nov. 28, 2007, which in turn claims priority to U.S. Provisional Patent Application No. 60/876,247, filed Dec. 21, 2006, the disclosures of which are incorporated herein by reference.

TECHNICAL FIELD

The subject invention relates generally to optical methods for inspecting and analyzing semiconductor wafers and other samples. In particular, the subject invention relates to methods for obtaining depth profiles information about the thermal and electronic properties, damage and defects in semiconductor wafers.

BACKGROUND OF THE INVENTION

There is a great need in the semiconductor industry for metrology equipment that can provide high resolution, non-destructive evaluation of product wafers as they pass through various fabrication stages. In recent years, a number of products have been developed for the nondestructive evaluation of semiconductor samples. One such product has been successfully marketed by the assignee herein under the trademark Therma-Probe (TP). This device incorporates technology described in the following U.S. Pat. Nos. 4,634,290; 4,646,088; 5,854,710; 5,074,669 and 5,978,074. Each of these patents is incorporated herein by reference.

In the basic device described in the patents, an intensity modulated pump laser beam is focused on the sample surface for periodically exciting the sample. In the case of a semiconductor, thermal and plasma waves are generated in the sample that spread out from the pump beam spot. These waves reflect and scatter off various features and interact with various regions within the sample in a way that alters the flow of heat and/or plasma from the pump beam spot.

The presence of the thermal and plasma waves has a direct effect on the reflectivity at the surface of the sample. As a result, subsurface features such as damage produced by ion implantation, defects and non-uniformity of carrier concentration, alter the passage of the thermal and plasma waves and have a direct effect on the optical reflective patterns at the surface of the sample. By monitoring the changes in reflectivity of the sample at the surface, information about characteristics below the surface can be investigated.

In the basic device, a second laser is provided for generating a probe beam of radiation. This probe beam is focused collinearly with the pump beam and reflects off the sample. A photodetector is provided for monitoring the power of reflected probe beam. The photodetector generates an output signal that is proportional to the reflected power of the probe beam and is therefore indicative of the varying optical reflectivity of the sample surface. The output signal from the photodetector is filtered to isolate the changes that are synchronous with the pump beam modulation frequency. A lock-in detector is typically used to measure both the in-phase (I) and quadrature (Q) components of the detector output. The two channels of the output signal, namely the amplitude $A^2 = I^2 + Q^2$ and phase $\Theta = \arctan(I/Q)$ are conventionally referred to as the Modulated Optical Reflectance (MOR) or Thermal Wave (TW) signal amplitude and phase, respectively.

Dynamics of the thermal- and carrier plasma-related components of the total MOR signal in a semiconductor is given by the following general equation:

$$\frac{\Delta R}{R} = \frac{1}{R}\left(\frac{\partial R}{\partial T}\Delta T_0 + \frac{\partial R}{\partial N}\Delta N_0\right)$$

where $\Delta T_0$ and $\Delta N_0$ are the temperature and the carrier plasma density at the surface of a semiconductor, R is the optical reflectance, dR/dT is the temperature reflectance coefficient and dR/dN is the carrier reflectance coefficient. For silicon, dR/dT is positive in the visible and near-UV part of the spectrum while dR/dN remains negative throughout the entire spectrum region of interest. The difference in sign results in destructive interference between the thermal and plasma waves and decreases the total MOR signal at certain experimental conditions. The magnitude of this effect depends on the nature of a semiconductor sample and on the parameters of the photothermal system, especially on the pump and probe beam wavelengths.

In the early commercial embodiments of the TP device, both the pump and probe laser beams were generated by gas discharge lasers. Specifically, an argon-ion laser emitting a wavelength of 488 nm was used as a pump source. A helium-neon laser operating at 633 nm was used as a source of the probe beam. More recently, solid state laser diodes have been used and are generally more reliable and have a longer lifetime than the gas discharge lasers. In the current commercial embodiment, the pump laser operates at 780 nm while the probe laser operates at 670 nm. The performance of this commercial TP system was significantly improved recently by the introduction of fiber-coupled diode lasers. Examples of the fiber-coupled TP system are given in the U.S. Pat. No. 7,079,249 assigned to the assignee of the current invention and incorporated herein by reference.

In modern semiconductor manufacturing, product wafers pass through multiple processing steps. Different parameters of product wafers are usually monitored after each process step in order to ensure that this particular fabrication step has been performed within specification. Different characteristics of semiconductor wafer are measured. After the two initial processing steps—ion implantation and annealing—several parameters are usually monitored that characterize damage density and electronic properties of the wafer, i.e., ion implantation dose and energy before anneal, active ion concentration, carrier lifetime, carrier mobility, wafer resistivity, etc. after anneal.

In most of these characterizations, uniform or discontinuously inhomogeneous material properties are assumed. This approach significantly simplifies quantitative analysis of the samples at the expense of the accuracy of such measurements. Except for a few situations when this simplifying assumption is valid and provides acceptable results, in most of the cases a continuously inhomogeneous profile of semiconductor material parameters should be considered for the adequate metrology analysis.

As an example, FIG. 1 shows several concentration depth profiles corresponding to different process conditions in manufacturing of semiconductor devices. In this figure, profiles 1 to 4 have been obtained using SIMS (Secondary Ion Mass Spectrometry) from ion-implanted Si wafers that underwent thermal annealing at different temperatures. In an ideal process, all these profiles would have been box-like, e.g., exhibiting an almost instant drop in concentration after the peak. However, such is not the case in real semiconductor manufacturing and profile information should be extracted from the sample for the accurate analysis of its characteristics.

A very limited number of technologies (such as SIMS, RBS—Rutherford Back Scattering, RS—spreading resistance, and others) are used today for parameter depth profiling in semiconductor manufacturing process. SIMS is primarily used to profile carrier concentration while RBS is used for profiling defects in semiconductors induced by ion implantation process. All these techniques are expensive, slow and destructive, i.e., require a special blank monitor wafer for analysis. In addition, production SIMS tools can not currently provide reliable concentration profile information below 100 A. Spreading resistance measurements are faster than SIMS and RBS but not accurate enough in its depth profiling capability. Also, RS technology requires good electrical contacts on both sides of semiconductor wafer which is not possible in most practical situations.

Therefore, there is a need for a fast, reliable non-destructive and non-contact technology capable of providing accurate depth profile information. Non-contact optical methods, such as MOR, are fast, accurate and reliable for characterizing of semiconductors and thin films on semiconducting materials. Thus, it would be desirable to develop an optically-based technology for depth profiling analysis of thermal and electronic properties of semiconductor wafers.

Photothermal and photoacoustic methods have long been used for characterization of different types of materials including semiconductors. In the past, there have been several attempts to use photothermal (a.k.a. opto-thermal) technologies for depth profiling of thermal and electronic properties in semiconductors.

Generally, performing depth profiling requires finding solutions to both forward and inverse problems. The forward problem is usually a theoretical model that takes into account all relevant properties of the sample (including their depth profiles, if needed) and experimental conditions to obtain an accurate description of the physical processes. The solution to the forward problem is a model predicting the signal behavior in practical measurements. The inverse problem is a reverse of the forward problem, e.g., it deals with obtaining sample parameters (including depth profiles) from the results of the experimental measurements. The solution to the inverse problem often involves sophisticated mathematical procedures, fitting algorithms, etc. and, therefore, is usually much more difficult to solve than the forward problem. Finding a solution to the inverse problem, especially for depth profiles in semiconductors, represents the biggest challenge in metrology.

In the past, there were numerous studies of the forward part of the depth profiling problem, especially in the thermal wave domain (e.g., in non-semiconducting materials) while only few studies were performed on the inverse problem in semiconductors.

The first conceptual study of MOR depth profiling capability in semiconductors is described in the article "Thermal and plasma wave depth profiling in silicon", by J. Opsal and A. Rosencwaig, Appl. Phys. Lett. 47(15), pp. 498-500 (1985), incorporated herein by reference. In this article, the plasma wave dependency on modulation frequency is used to probe semiconductor material at different depths potentially leading to the reconstruction of electronic parameter depth profiles. However, only a two-layer semiconductor sample was discussed in this article to illustrate depth profiling using the plasma wave component of MOR signal. In addition, the solution to the inverse problem was not proposed in this study.

Several studies related to thermal and electronic parameter depth profiling including both forward and inverse problems using Photothermal Radiometry (PTR) technique have been performed by A. Mandelis and his group at the University of Toronto and described in two publications. Thermal diffusivity depth profiling concept is presented in the article "Generalized methodology for thermal diffusivity depth profile reconstruction in semi-infinite and finitely thick inhomogeneous solids", by A. Mandelis, F. Funak, and M. Munidasa, J. Appl. Phys. 80(10), pp. 5570-5579 (1996), and depth profiling of electronic parameters in semiconductors using PTR is described in the article "Hamiltonian plasma-harmonic oscillator theory: Generalized depth profilometry of electronically continuously inhomogeneous semiconductors and the inverse problem", by A. Salnik and A. Mandelis, J. Appl. Phys. 80(9), pp. 5278-5288 (1996). Both papers are incorporated herein by reference.

In these papers, the Hamiltonian-Jacobi formalism of the propagation of the thermal and plasma waves in continuously inhomogeneous semiconductors is presented and a reconstruction of thermal diffusivity (thermal properties) and carrier lifetime (electronic properties) depth profiles is demonstrated. The solutions to the inverse problem in both cases (thermal and plasma parameters) were based on modulation frequency dependencies of the PTR signal. Thermal diffusivity depth profiles were successfully calculated from the experimental data while carrier lifetime depth profiles were only partially determined. This was due to the very specific nature of the plasma waves: these waves are frequency-independent at low modulation frequencies when $\omega\tau \ll 1$ and they are lifetime-independent at high modulation frequencies when $\omega\tau \gg 1$, while thermal waves are both frequency and thermal diffusivity-dependent at all modulation frequencies. This fundamental limitation of plasma waves makes it impossible to use frequency domain measurements for electronic parameter depth profiling in semiconductors.

Another attempt to solve the inverse problem in depth profiling of ultra-shallow junctions (USJ) formed in semiconductor materials is presented in the article "Carrier illumination for characterization of ultra-shallow doping profiles", by T. Clarysse, et al., Book of Abstracts, 7th Int. Workshop on: Fabrication, Characterization, and Modeling of USJ Doping Profiles in Semiconductors (USJ-2003), Santa Cruz, Calif., Apr. 27-May 1, 2003, pp. 321-327, incorporated herein by reference. In this paper, an MOR-like experimental system was used to obtain signal dependencies on pump beam power. A solution to the inverse problem was not discussed in this publication. However, FIG. 2 herein schematically illustrated two box-like approximations to the real concentration profiles of the type that could have been used by Clarysse to create a simplified theoretical model for obtaining concentration depth profiles. As shown in FIG. 2, these box-like approximations (discontinuously inhomogeneous approximations), being relatively easy to invert, provide only a zero-order approximation to the real profile shape (continuously inhomogeneous). Therefore, box-like profiles can not be used for the accurate reconstruction of depth profiles.

To summarize, the current state of the art in depth profiling of continuously inhomogeneous electronic properties in surface modified semiconductors (i.e., ion-implanted Si and USJ) concentrates on solving only the forward part of the problem. A very few attempts to solve the inverse part of this depth profiling problem have failed to provide an accurate, reliable and sensitive enough technique that is required for applications in modern semiconductor manufacturing.

DETAILED DESCRIPTION OF THE PREFERRED EMBODIMENTS

The present invention provides two different methods for depth profiling of parameters of interest in semiconductor materials using the MOR methodology. The first method is based on a simple reconstruction of the approximate depth profiles using experimental parameter values measured at certain depths below the surface of a sample. The second technique is a full forward and inverse problem method that utilizes MOR signals obtained by varying the experimental parameters such as different lateral beam offset distances (pump and probe beam separations), different modulation frequencies and/or different pump and probe beam wavelengths.

Apparatus Description

Figure 3:
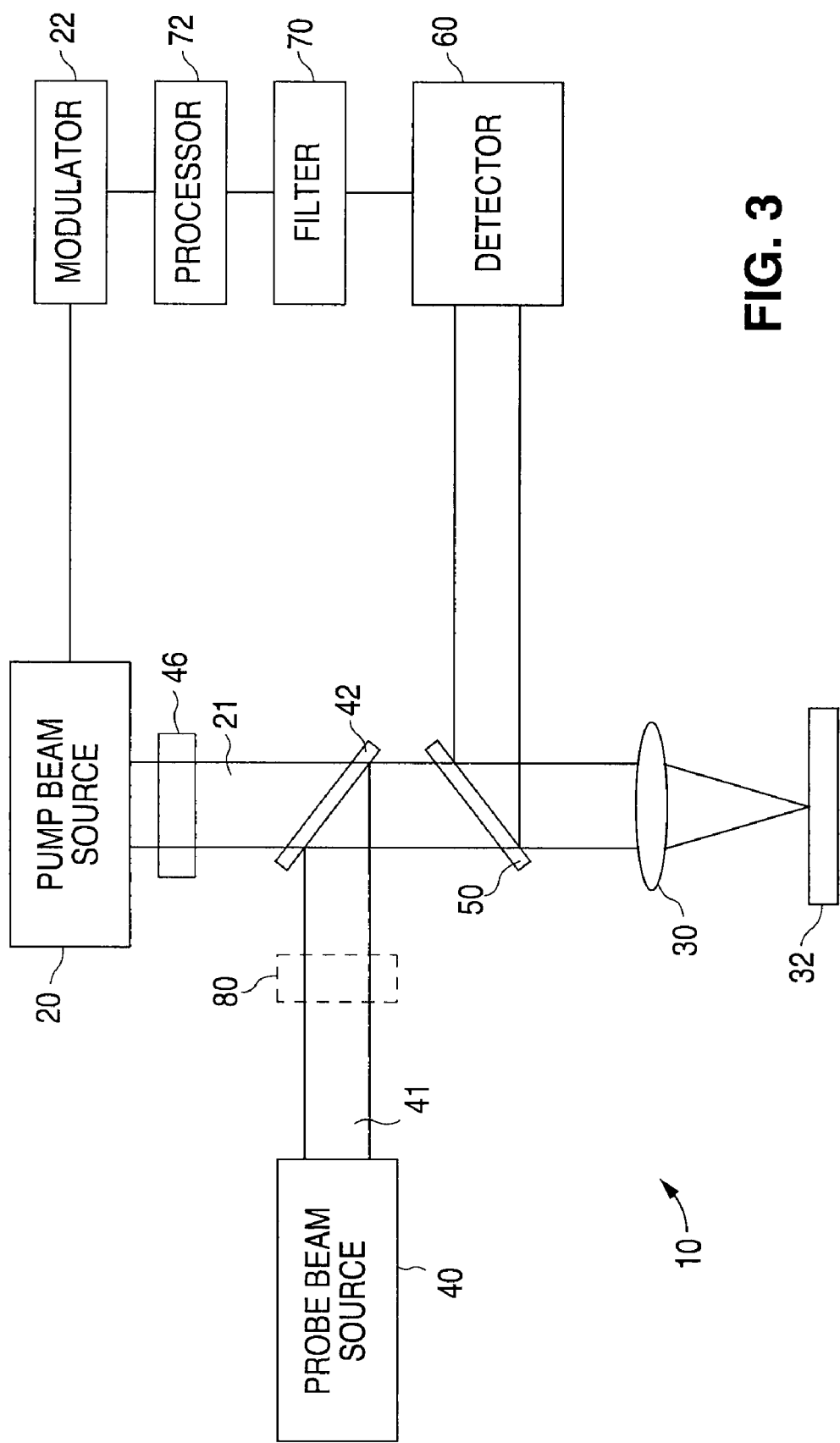
FIG. 3 is a block diagram of a modulated optical reflectivity (MOR) apparatus for use in the methods of the subject invention.

A schematic diagram of the MOR system capable of obtaining the measurements necessary to perform the methods of the subject invention is illustrated in FIG. 3.

System 10 includes a light source 20 for generating a pump beam of radiation 21. Pump beam source may be an intensity modulated laser or incoherent light source. Gas, solid state or semiconductor lasers can be used, including laser systems coupled with a fiber. For methods which require tuning the wavelength of the pump beam, a broadband tunable source is preferable. The pump beam induces a modulation of the optical characteristics of the sample which may be due to the generation of the thermal and plasma waves affecting the optical properties of the sample. The pump beam is intensity modulated at a predetermined frequency, selected upon the desired experimental conditions. In some cases, the pump beam modulation frequency can be varied to obtain additional data.

In one preferred embodiment, the pump source is a laser. The laser is intensity modulated by a drive signal supplied by a modulator 22. The modulation frequency can vary from a few hertz to tens of megahertz. In one preferred embodiment, the modulation frequency is on the order of one megahertz. This is a frequency which will create plasma waves in a typical semiconductor the sample.

A lens 30 focuses the pump beam 21 onto the sample 32. The pump beam spot size on the sample may be from 0.5 μm to 10 μm.

The probe beam source 40 is used to generate a probe beam of radiation 41. The light source is typically a laser. For spectroscopic measurements, a tunable laser can be used. In the alternative, a broadband or white light source with a filter can be used to generate the probe beam. The probe beam is directed towards the lens 30 by beam splitter/combiner 42. The probe 41 is focused onto the sample 32 using lens 30. The lens 30 is positioned to create a probe beam spot on the sample from 0.5 μm to 10 μm. Both pump and probe beams may be used at a normal incidence with respect to the surface of the sample or at an angle.

In FIG. 3, the probe beam spot is illustrated to be coincident with the pump beam spot on the sample. In accordance with the subject invention, at least one beam tracker 46 is provided in the path of either the pump or probe beams for adjusting the relative positions of the pump and probe beams on the sample. The tracker 46 can be used to vary the lateral offset of the beams for obtaining multiple MOR measurements.

The reflected probe beam is deflected by the beam splitter/combiner 50 and is measured by a detector 60 which is configured to be underfilled so that the output signal corresponds to the reflected beam power.

Figure 1:
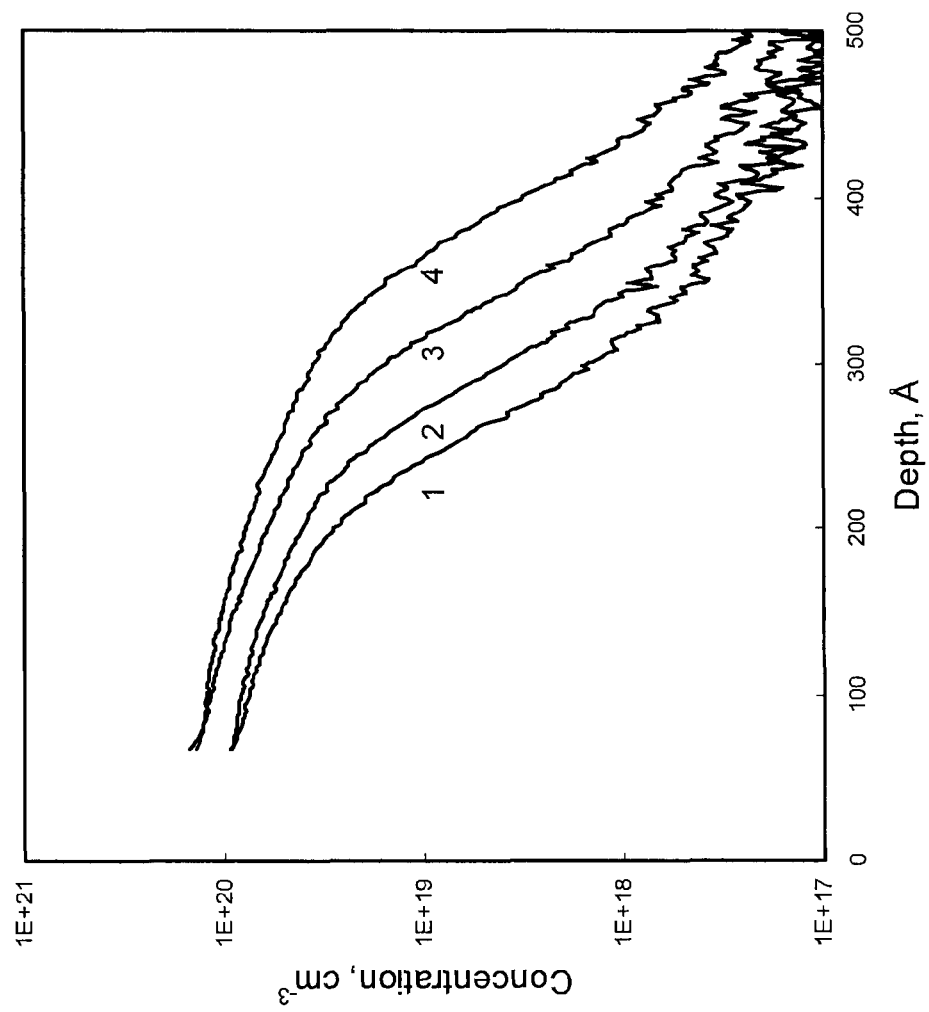
FIG. 1 is a graph illustrating several concentration depth profiles corresponding to different process conditions in manufacturing of semiconductor devices.
Figure 2:
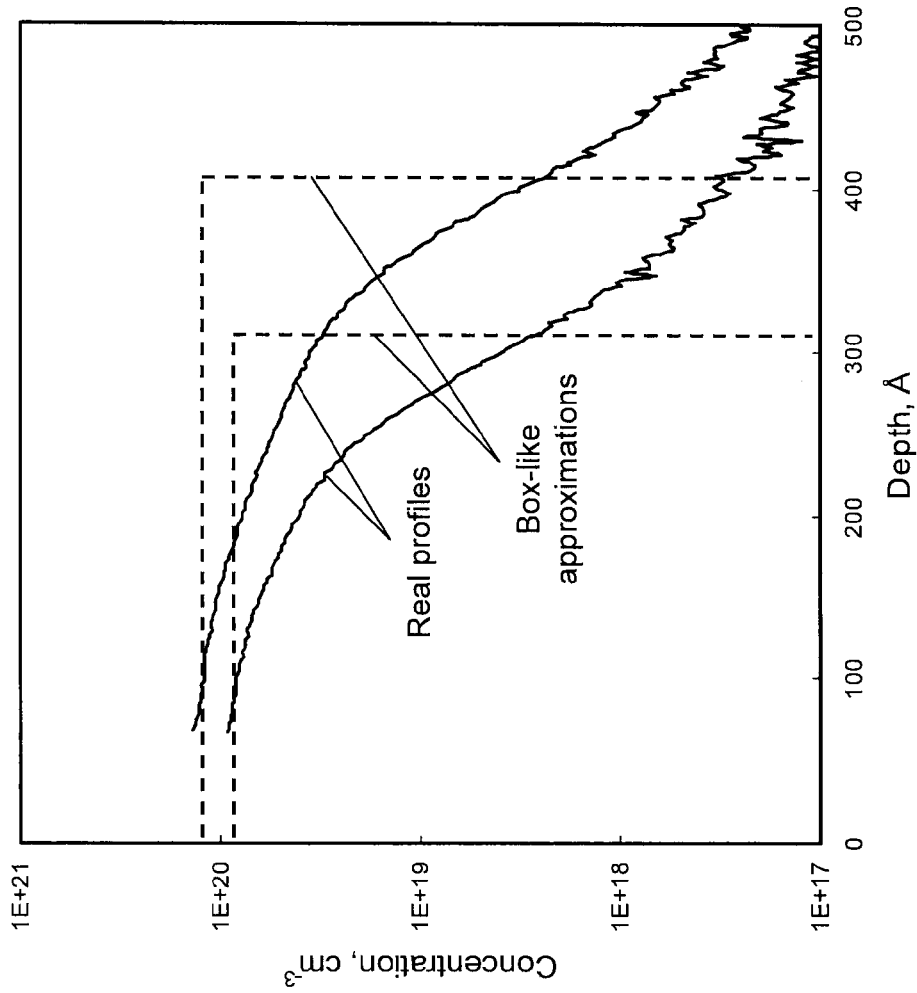
FIG. 2 is a graph illustrating two box-like approximations compared to real world dopant concentration profiles.

The output signal from the detector 60 is passed to a filter 70 for isolating the beam intensity changes that are synchronous with the pump beam modulation frequency. For most implementations, filtering is performed using a heterodyne or lock-in detector (See U.S. Pat. No. 5,978,074 and, in particular, FIG. 2 for a discussion of such a lock-in amplifier/detector). As noted above, the outputs from a lock-in are the in-phase (I) and quadrature (Q) components of the detector output.

The signals from filter 70 are sent to processor 72 for analysis. The processor can use the outputs to calculate MOR amplitude and phase. Also, information about the sample can be determined directly from the I and Q signals.

Parameter-Based Depth Profiling Reconstruction Method

Figure 4:
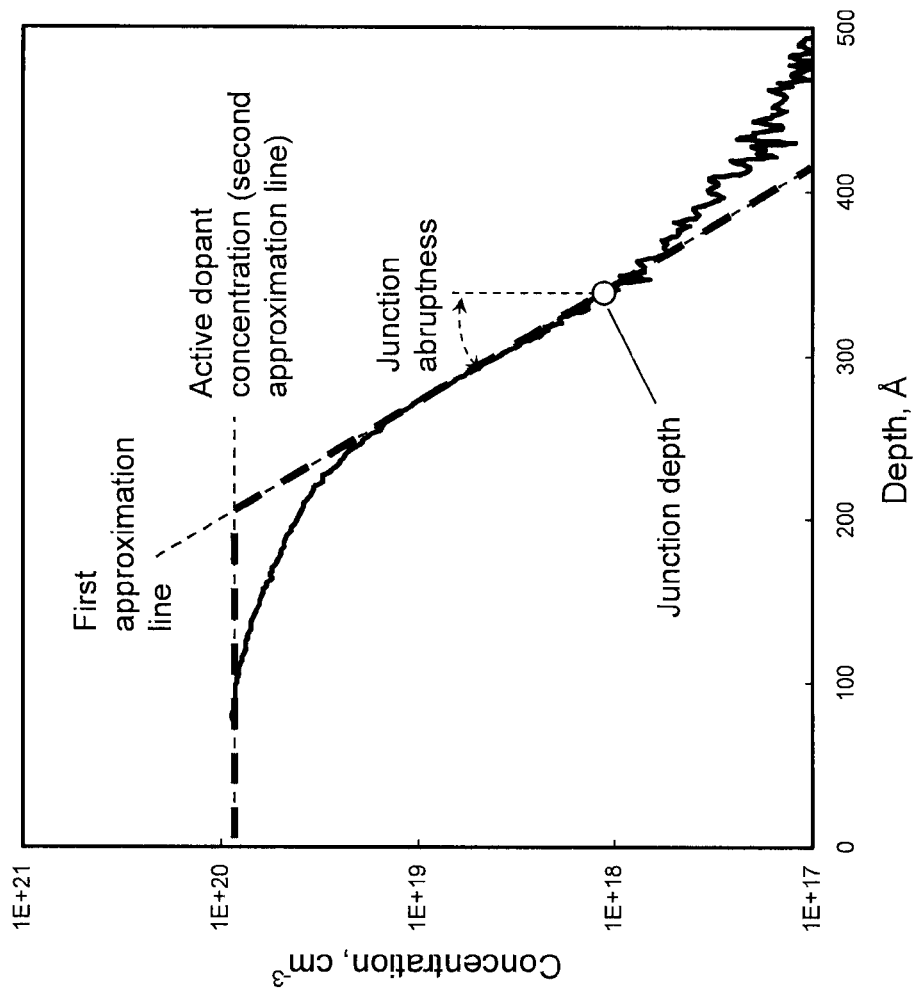
FIG. 4 is a graph illustrating the construction of a dopant depth profile using a combination of measurements.

This method is based on measuring certain characteristics of the sample and combining them into a simple reconstructed depth profile. FIG. 4 shows schematically how this method may be applied to the reconstruction of the active carrier concentration depth profiles in USJ samples. The parameter-based depth profile reconstruction method consists of three steps.

First, a junction depth (marked by an open circle in FIG. 4) in USJ wafer is measured using the MOR technology. This depth measurement may be performed in a variety of ways. In a preferred embodiment, the Q-component of the MOR signal is measured on an USJ sample and compared to pre-determined Q-components values for samples with known USJ depths to obtain the actual USJ depth value. The modulation frequency in these MOR experiments is preferably set to 1 MHz or higher to ensure high sensitivity and rich information content of the MOR signal. MOR amplitude and/or phase data may also be used for USJ depth measurements in a way similar to MOR technology applications to ion implant characterization described in the Invention Background section of the current application. A method for measuring USJ depth using Q-component of the MOR signal is described in the U.S. Pat. No. 7,248,367 assigned to the assignee of the present invention and incorporated herein by reference.

Once the USJ depth value is obtained, it defines the first point of the depth profile curve as shown in FIG. 4. The corresponding concentration value (vertical position of the open circle in FIG. 4) depends on the pre-determined USJ values measured by an independent technology (usually SIMS). USJ depth in SIMS measurements is usually defined at the ion concentration level of $10^{18}$ cm$^{-3}$ as shown in FIG. 4.

The second step of this depth profiling approach is related to the measurement of USJ profile abruptness in the same sample. The MOR technique is well suited for this task and is able to accurately and non-destructively measure USJ profile abruptness using different lateral offsets between the pump and probe beams and Q-I signal processing. The method and system for measuring USJ profile abruptness in USJ using the MOR technology is described in the above cited U.S. Pat. No. 7,248,367. In this method, to measure the USJ profile abruptness, a MOR-type metrology tool is used to performed a series of two or more measurements, each with a different pump-probe beam lateral separation distances (offsets). Quadrature (Q) and In-Phase (I) components of the MOR signal are obtained for each measurement and used to derive a line in the Q-I space. An abruptness measurement is derived by comparing the line slope to a similar line slope obtained from calibration samples with known USJ profile abruptness.

With the USJ profile abruptness determined as described above, a slope approximating the shape of the deeper part of the USJ depth profile can be drawn as illustrated in FIG. 4 by the first approximation dotted line. In calibration samples, USJ profile abruptness (usually measured by SIMS) is determined as a slope of the profile between the ion concentration values of $10^{18}$ cm$^{-3}$ and $10^{19}$ cm$^{-3}$. Therefore, the USJ abruptness and the USJ depth determined in the first step define a unique line having a slope equal to USJ abruptness and crossing the point of USJ depth at the ion concentration level of $10^{18}$ cm$^{-3}$ as shown in FIG. 4. This line provides a good approximation to the shape of the deeper part of the USJ depth profile.

Finally, the active dopant concentration (a.k.a. peak carrier concentration) of the same sample is measured using the MOR technology as described in the U.S. Patent Publication No. 2006/0166385, assigned to the assignee of the present invention and incorporated herein by reference. In this method, the Q and I components of the MOR signal are measured and compared to the corresponding calibrated values in the Q-I space. The active dopant concentration is derived from the position of the line in Q-I space relative to the position of the lines corresponding to samples with known concentration values. This linear correlation between the Q and I components of the MOR signal is unique for high modulation frequencies MOR experiments when the propagating plasma and thermal waves are created in the semiconductor sample.

Once the active carrier (dopant) concentration is measured, a horizontal line can be drawn on the concentration vs. depth plot (the second approximation dotted line in FIG. 4), thus completing the reconstruction of the approximated concentration depth profile.

As it is shown in the above referenced patent documents and in the article "Towards non-destructive carrier depth profiling", by T. Clarysse, W. Vandervorst, M. Bakshi, L. Nicolaides, A. Salnik, and J. Opsal, J. Vac. Sci. Technol. B. 24(3), pp. 1139-1146 (2006), USJ depth, abruptness and active carrier concentration can be obtained simultaneously using MOR technology. Lateral beam separation (offset) experiments required for USJ abruptness measurements can be easily achieved by in the current commercial Therma-Probe instrument.

Other methods of obtaining additional MOR measurement data include varying the wavelength of the pump and/or probe beam and varying the modulation frequency of the probe beam. These approaches can be used in various combinations to facilitate the depth profile reconstruction described herein.

In the prior art references discussed above, all parameters characterizing USJ were obtained and treated separately in the analysis of the junction quality and performance of the semiconductors processing steps. The parameter-based depth profiling method of the present invention combines the separate pieces of data into a single graphical representation of the junction shape, e.g., its depth profile. This depth profile may be displayed on the screen of a metrology system and/or stored in memory for further analysis and comparison.

The parameter-based depth profile reconstruction method of this invention can be applied not only to reconstruction of the active dopant concentration (peak carrier concentration) depth profiles as illustrated above, but also in other depth profiling applications such as damage depth profiles in semiconductor samples after the ion implantation and other applications. In these cases, one skilled in the art should be able to find characteristic points and slopes as well as means to measure them allowing for the reconstruction of a depth profile that is close to the profile revealed by destructive techniques such as SIMS and RBS.

Figure 5:
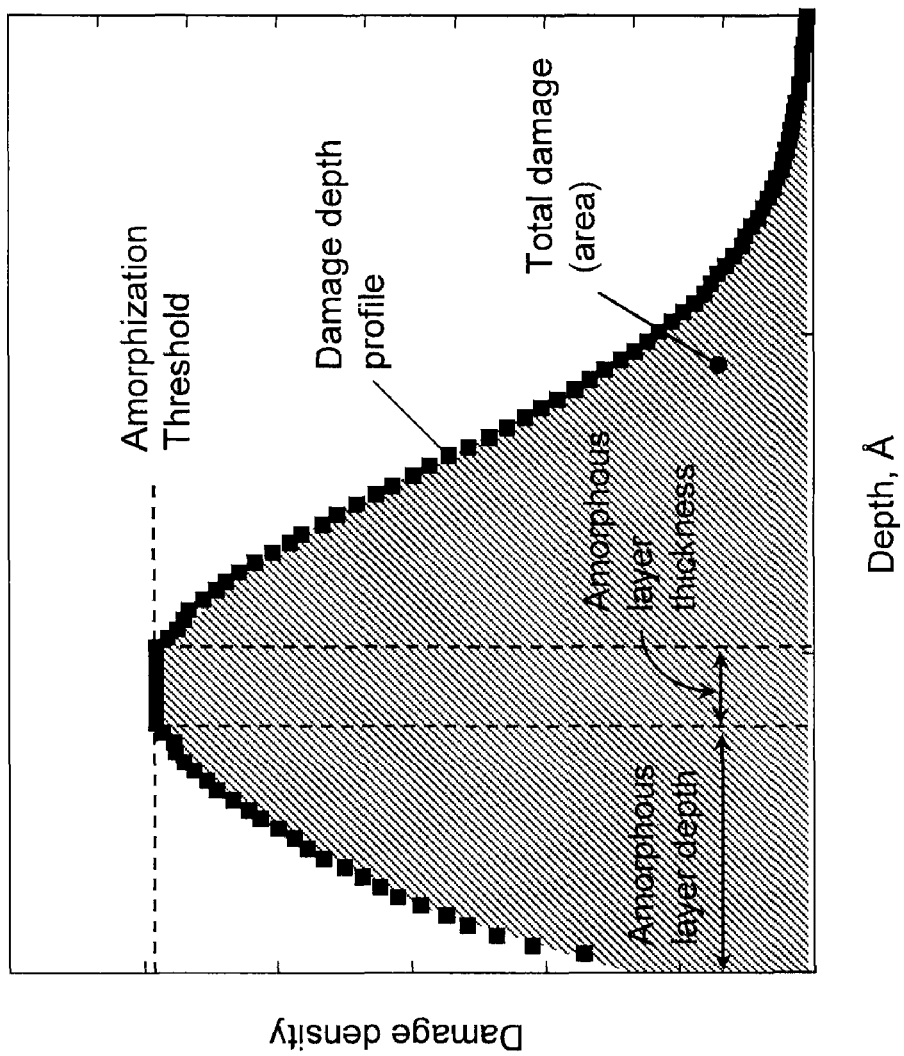
FIG. 5 is a graph illustrating the construction of a damage depth profile using a combination of measurements.

An additional example is illustrated in FIG. 5. More specifically, FIG. 5 schematically illustrates a set of parameters that identify the approximate damage depth profile in ion implanted semiconductors. The amorphous layer thickness, represented by a pair of dotted vertical lines, can be obtained by calibration of the MOR signal amplitude to that obtained from a reference samples with known amorphous layer thickness. The amorphization threshold (top horizontal line) and amorphous layer depth (distance from the sample surface to the first vertical line) are usually known values for any given implantation species and implantation energies. In the case where the maximum damage in a profile is below the amorphization threshold (no distinct amorphous layer formed), the top horizontal line can be drawn based on the measured implantation dose. The total damage (area under the damage depth profile) is directly proportional to the MOR signal amplitude as shown in inventors' prior publication (A. Salnik, et. al. J. Appl. Phys. Vol. 91, No. 5, page 2874, March 2001). These separate parameters, specifically, amorphous layer thickness, threshold, layer depth and total damage can be used to construct a profile of the type shown in FIG. 5.

Full Forward and Inverse Problem Depth Profiling Method

This method is based on measuring the MOR signal dependencies on variables including the pump-probe beam separation distances (offsets), varying pump and probe beam wavelengths and varying pump beam modulation frequencies. This measured data is input to a theoretical model (forward problem) and regressed (inverse problem) to obtain a depth profile of interest.

As we pointed out earlier, the conventional approach to the depth profiling problem in semiconductor samples using the modulation frequency scans is limited in its ability to accurately reconstruct the electronic parameter depth profiles because of a special nature of the plasma waves. In the present invention, the MOR signal Q- and/or I-components dependencies on pump-probe beam offsets and/or wavelengths are used instead of, or in conjunction with, the pump beam modulation frequency scans. The use of offset scans can provide an information rich signal that can be utilized for the depth profile reconstruction in the solution to the inverse problem.

The use of MOR offset scans for characterization of different properties of conductive and layered materials is described in the U.S. Pat. Nos. 5,978,074; 6,191,846; 6,320,666; 6,453,685; 6,522,413, and 6,836,338 assigned to the assignee of the present invention and incorporated herein by reference. In these patents, the MOR signal amplitude and/or phase are measured as a function of the pump-probe beam lateral separations at different modulation frequencies and the resulting dependencies are used to determine properties of the sample. The technique described in these patents primarily addresses the problem of measuring the thicknesses of metal layers on the semiconductor substrates using the thermal waves. However, this set of prior art documents fails to disclose the application of the MOR offset scanning to the analysis of semiconductor materials with both thermal and plasma waves present in the sample. In addition, the technique of these does not take advantage of the MOR signal processing in the Q-I space that is more informative than just MOR amplitude or phase. Finally, the method of these prior art patents does not address and can not be applied to the problem of electronic (plasma) parameters depth profiling in semiconductors.

For the inverse depth profiling problem to be solved accurately, high quality and high sensitivity experimental data should be obtained. In the MOR signal in semiconductors, the region of the plasma-thermal interference is the most sensitive to variations in the thermal and electronic parameters. A good analogy here would be observing a fine structure of the sun (spots, etc.) with a filter that significantly reduces the intensity of the sun's radiation allowing one to see a fine structure of that otherwise very bright light source. In a similar manner, plasma-thermal interference reduces the magnitude of the plasma and thermal waves in semiconductors revealing the fine details of the electronic and thermal properties of the sample including the depth profiles.

The method and system utilizing the Controlled Plasma-Thermal Interference (CPTI) to enhance the sensitivity in MOR measurements of implanted semiconductors is described in U.S. patent application Ser. No. 11/899,105, filed Sep. 4, 2007, assigned to the assignee of the present invention and incorporated herein by reference. In this method, the experimental parameters of the MOR system are adjusted to position the maximum of the plasma-thermal interference at the desired point in the MOR signal dependence on implantation dose to increase system's sensitivity and overall performance in dose measurements. This CPTI technique is aimed primarily at the implantation dose measurements and is not addressing the problem of the depth profiling.

Figure 6:
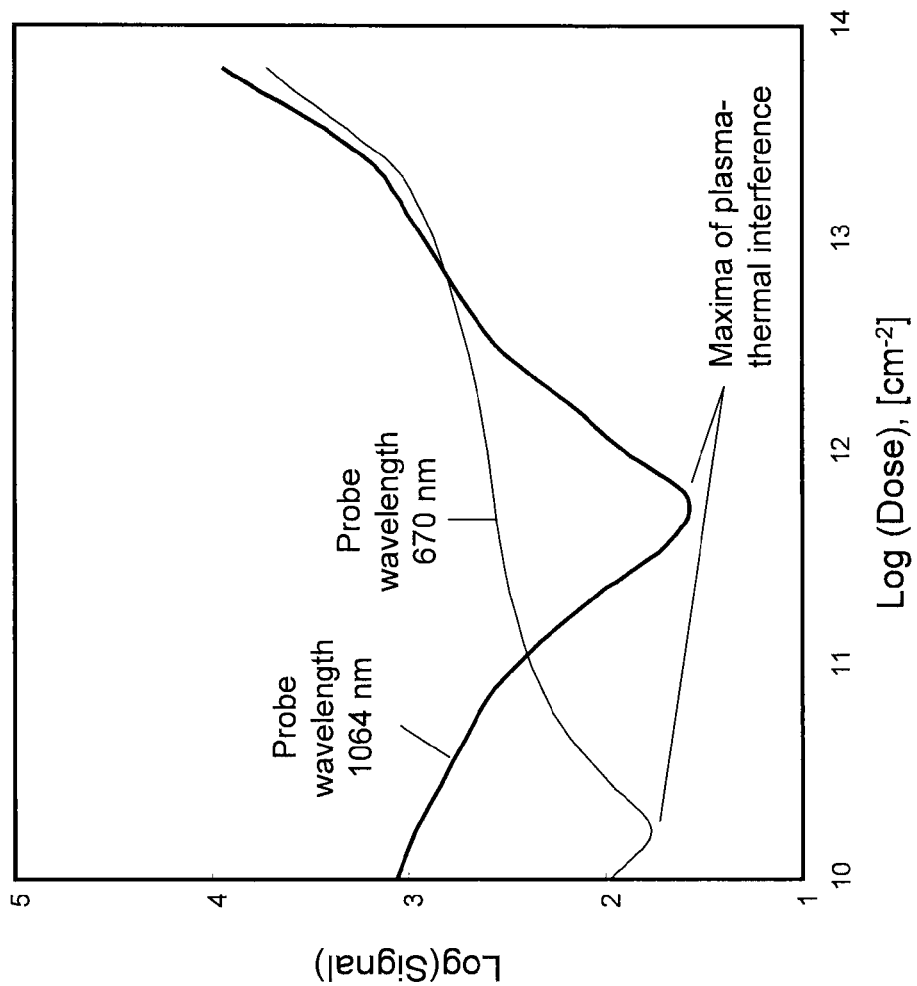
FIG. 6 is a graph illustrating the changes in plasma-thermal interference in the MOR signal for different wavelength probe beams.

The effect of the destructive plasma-thermal interference in the MOR signal from ion implanted semiconductors is shown in FIG. 6. The maxima of the MOR plasma-thermal interference are characterized by a pronounced minimum in the MOR signal amplitude dose dependencies. At the implantation doses below the region of maximum interference, the plasma waves dominate the MOR signal. At the doses above that region, the MOR signal is dominated by the thermal waves.

In FIG. 6, two maxima of plasma-thermal interference (minima in MOR signal) are shown for different probe beam wavelengths and the same pump beam wavelength. A longer probe beam wavelength shifts the position of the maximum interference to higher implantation doses. Therefore, the region of maximum plasma-thermal interference can be positioned at any given implantation dose by selecting the appropriate probe beam wavelength.

Figure 7:
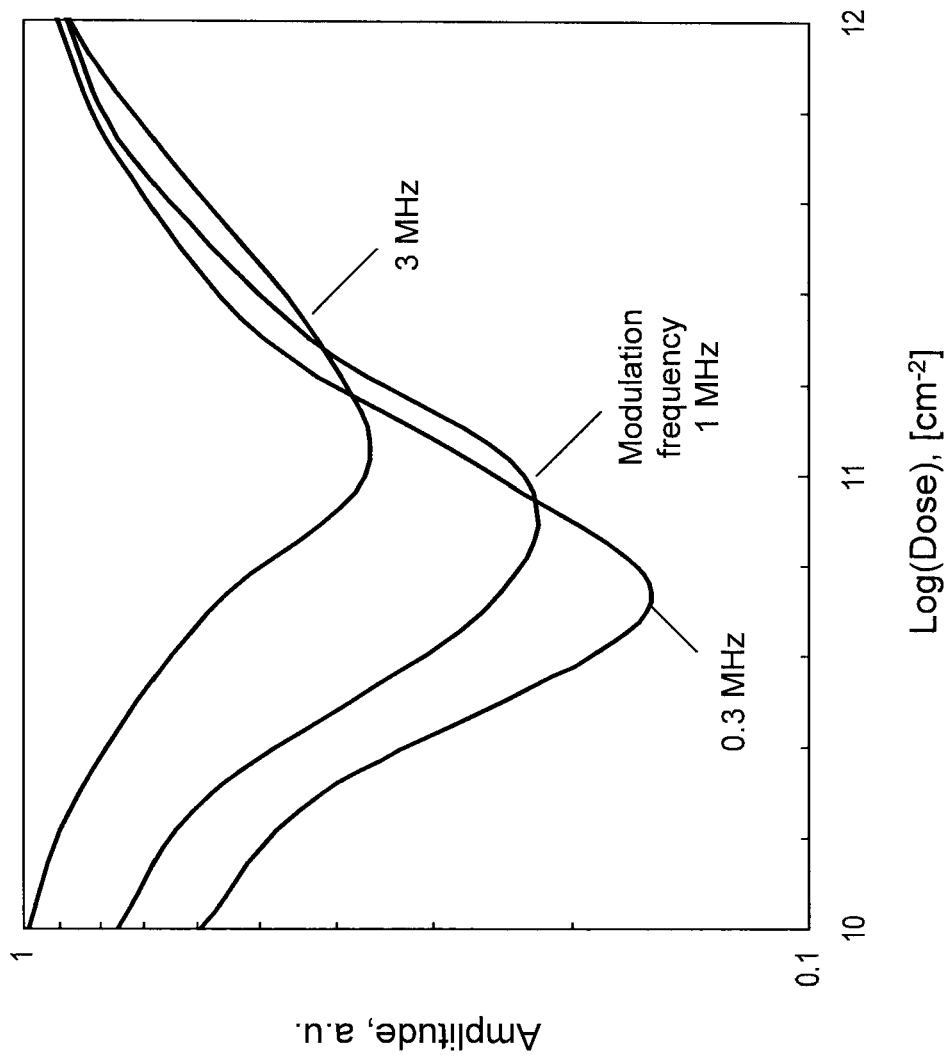
FIG. 7 is a graph illustrating the changes in plasma-thermal interference in the MOR signal for different pump beam modulation frequencies.

Changing the position of the region of maximum interference in MOR experiments may also be achieved by varying the modulation frequency. While the probe beam wavelength can be used to coarse-position the peak at the desired implantation dose, the fine tuning may be done by decreasing and increasing the pump beam modulation frequency. FIG. 7 shows the MOR amplitude dose dependencies in the region of maximum plasma-thermal interference modified by varying the modulation frequency from 0.3 MHz to 3 MHz. With increasing modulation frequency, the position of the maximum of the plasma-thermal interference is shifting to higher doses. The shape of the characteristic minimum in the MOR signal amplitude is also changing with modulation frequency from very deep to relatively shallow (FIG. 7).

Therefore, by selecting the appropriate experimental MOR measurement parameters, such as the pump and probe beam wavelengths, modulation frequency, etc.—it is possible to precisely position the region of the plasma-thermal interference at the desired dose range. It is also possible to modify the shape of the MOR signal in this region to optimize its sensitivity to thermal and electronic parameters of interest. In the preferred embodiment, the dose region of maximum plasma-thermal interference in MOR amplitude is defined as a plus-minus half order of magnitude from the implantation dose corresponding to the peak of the interference. That is if the MOR amplitude negative peak position is at the implantation dose of $10^{11}$ $cm^{-2}$, then the dose region of maximum plasma-thermal interference is from $5 \times 10^{10}$ to $5 \times 10^{11}$ $cm^{-2}$.

Setting the instrument parameters to maximize the plasma-thermal interference can also be useful in the first embodiment of the subject invention where reconstruction of the depth profile is achieved without using a modeling approach.

Figure 8:
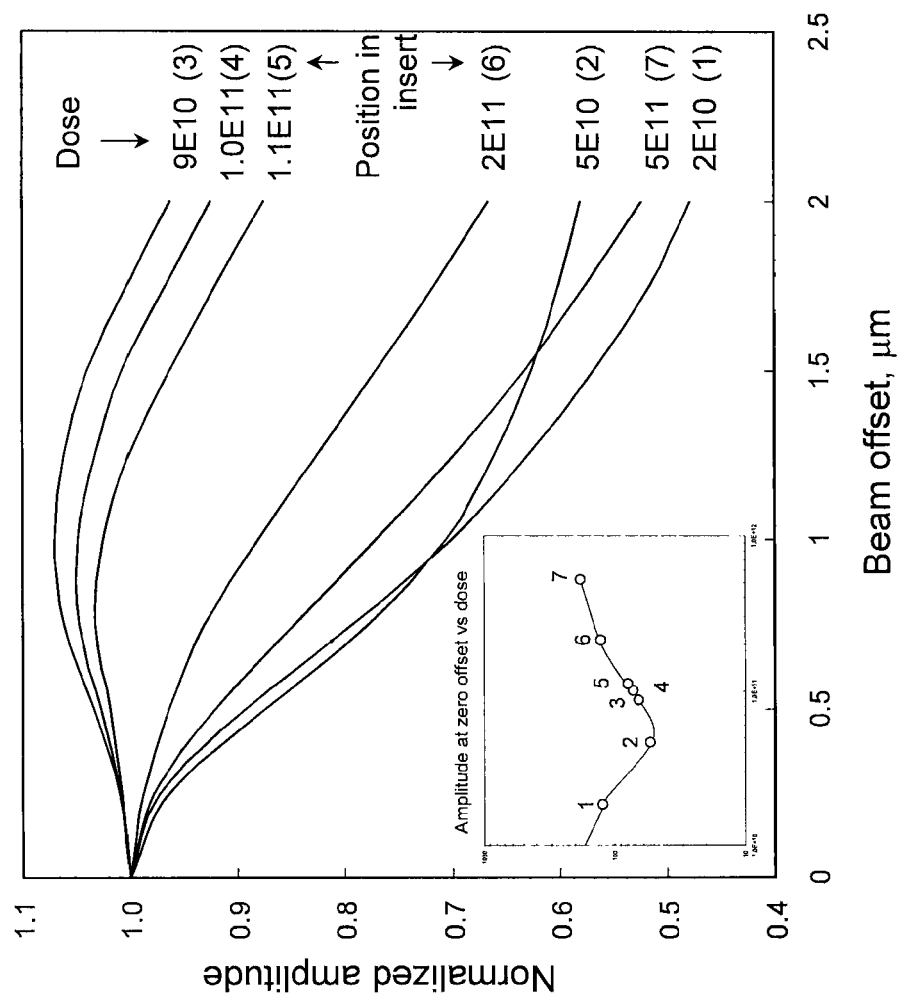
FIG. 8 is a graph illustrating MOR amplitude dependencies on various lateral beam offsets for a range of implantation doses
Figure 9:
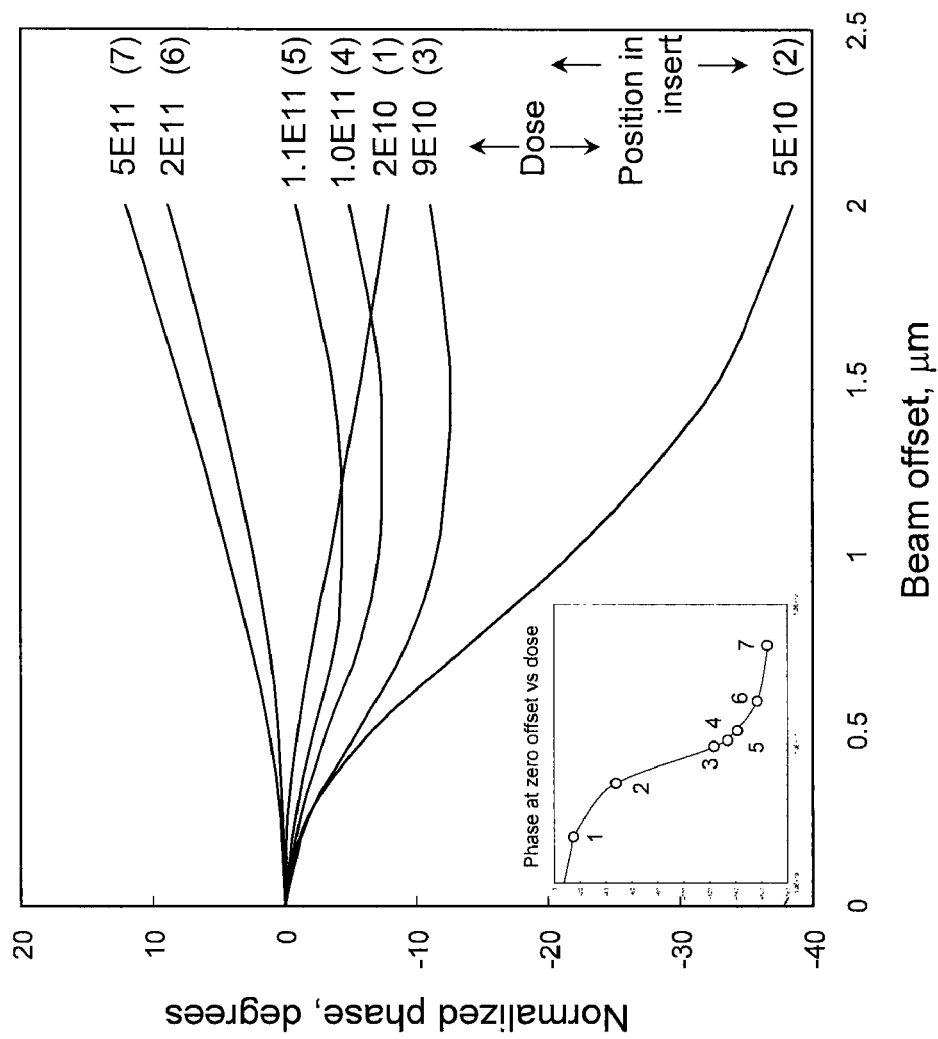
FIG. 9 is a graph illustrating MOR phase dependencies on various lateral beam offsets for a range of implantation doses.

The MOR pump-probe beam offset scans obtained from a range of implantation doses including the region of the maximum plasma-thermal interference exhibit different behavior depending on how far away from the region of maximum of interference this particular dose is located. FIGS. 8 and 9 respectively show experimental normalized MOR amplitude and for phase offset scans at different implantation doses located in the region of the maximum plasma-thermal interference. Inserts in both figures show the position of each particular dose relative to the maximum interference point. For the MOR amplitude offset scans (FIG. 8), the most dramatic changes in the shape occur between the implantation doses of $5 \times 10^{10}$ and $9 \times 10^{10}$ $cm^{-2}$ (points 2 and 3 in the insert). This is when the MOR signal is going through the peak of the plasma-thermal interference. Starting with the behavior characteristic associated with the pure plasma-dominated signal, the MOR amplitude becomes more intense at some offset distances different from the zero offset at the peak of plasma-thermal interference and gradually relaxes towards the pure thermally-dominated MOR response (points 1 to 7).

FIG. 9 shows similar behavior in the MOR phase which has its most significant changes between the point 1 and 2 (insert), e.g., ion implantation doses of $2 \times 10^{10}$ and $5 \times 10^{10}$ $cm^{-2}$. This is consistent with the typical photothermal experiments where the phase is ahead of the amplitude in sensing changing conditions in the material. Variations in modulation frequency (not shown in FIGS. 8 and 9) further modify the shape of the MOR amplitude and phase.

Figure 10:
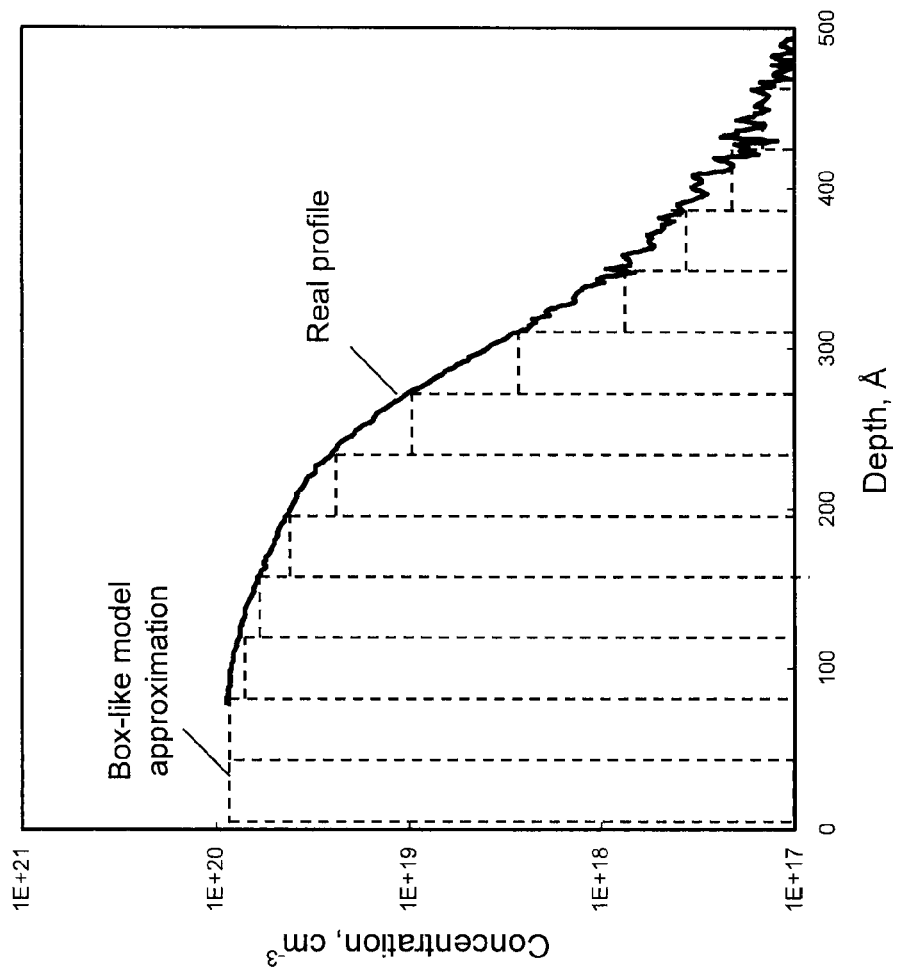
FIG. 10 is a graph illustrating a box-like approximation of dopant concentration as a function of depth that may used in a theoretical model for solving the forward problem.

For the solution to the forward problem, a theoretical model for the MOR signal response from a semiconductor sample is constructed that takes into account all experimental conditions—pump and probe beam wavelengths, modulation frequency, beam size, etc.—as well as an approximate depth profile of a parameter of interest. This theoretical model may be built in a variety of different ways. As an example, FIG. 10 schematically shows a box-like approximation that may be used in a theoretical model for the solution of the forward problem. In this approach, the shape of a real depth profile (carrier concentration in this case) is approximated by boxes of different height and equal thickness. By increasing the number of boxes (and, therefore decreasing the thickness of each box for a given depth range), any desired degree of precision in theoretical model can be achieved. However, increasing number of boxes leads to a significant increase in computational time required to find an acceptable numerical solution to the forward and inverse problems.

Figure 11:
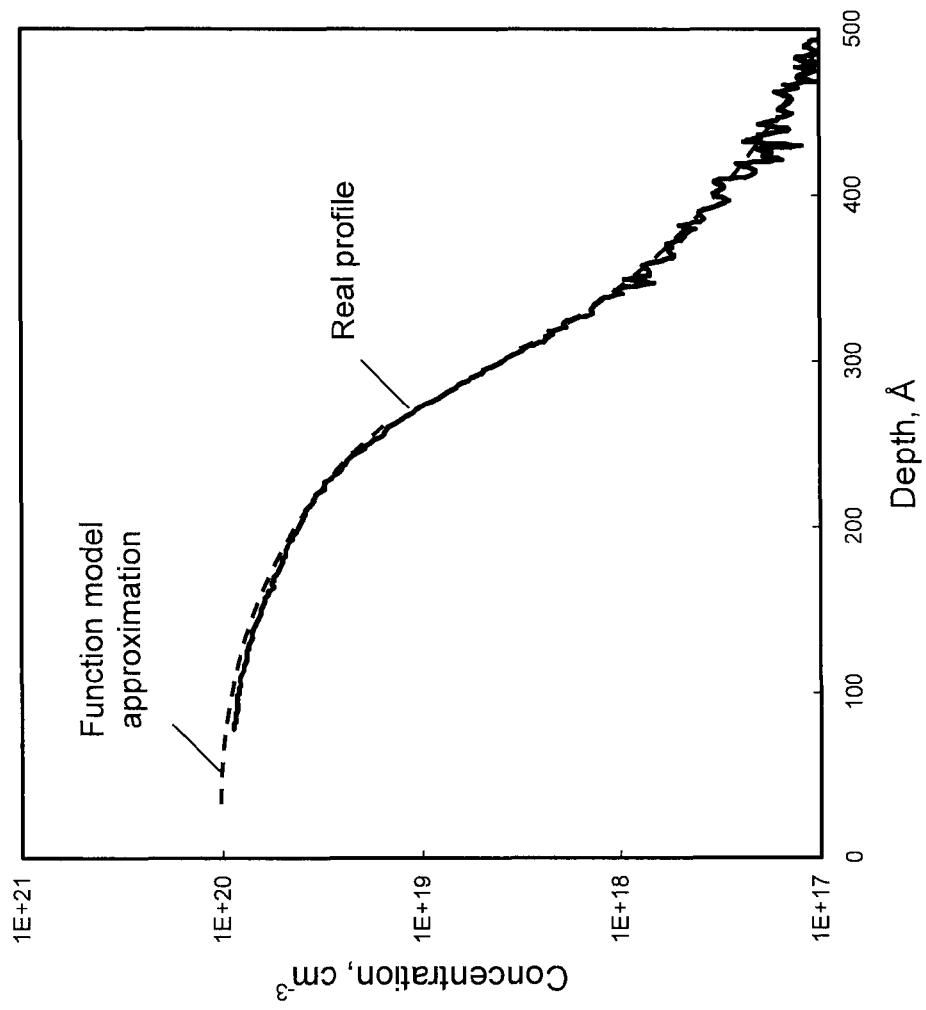
FIG. 11 is a graph illustrating a function based approximation of dopant concentration as a function of depth that may used in a theoretical model for solving the forward problem.

In the preferred embodiment, a function-approximated theoretical model is used to solve the forward and inverse depth profiling problems. Approximation of the real depth profile (carrier concentration) by the function model is shown schematically in FIG. 11. Here, the real concentration depth profile is approximated by an artificial function that is shaped according to the real profile by varying a set of function parameters. Examples of such function may include exponential terms, polynomial terms, etc. The main advantage of this approach compared to box-like approximations is in reduced number of independent variables used to adjust theoretical depth profile to match the real depth profile with an acceptable degree of precision.

However, the scope of the present invention is not limited to only the two types of theoretical models described above. One skilled in the art should be able to find other solutions that would adequately approximate a real depth profile in the sample.

Figure 12:
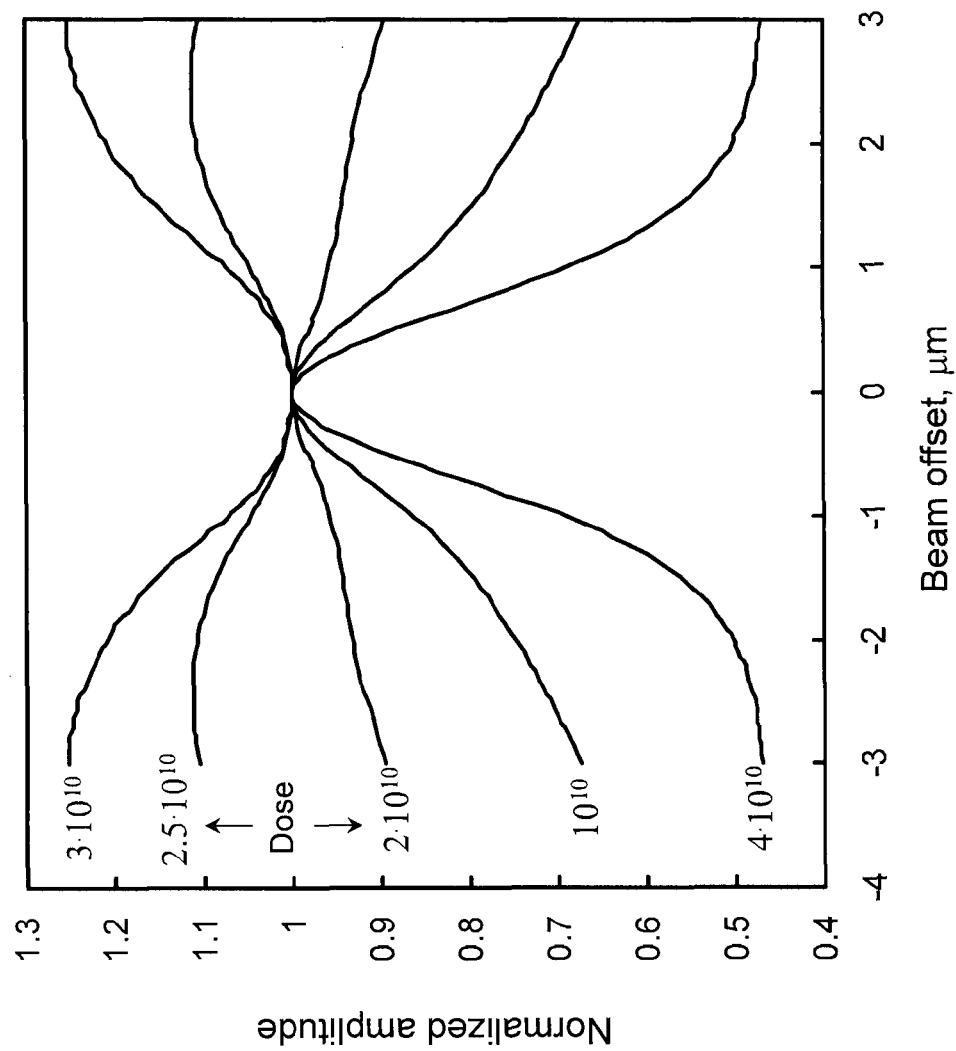
FIG. 12 is a series of MOR amplitude responses for different beam offsets and dopant concentrations calculated based on a theoretical model.

FIG. 12 shows theoretical normalized MOR amplitude offset scans calculated using the box-like approximated solution to the forward problem for a semiconductor sample implanted with different implantation doses. These theoretical dependencies may be compared to experimentally obtained scans shown in FIG. 8 (single-side scans). In this example, solving the inverse problem for the dopant depth profile will require varying parameters used to produce theoretical curves of FIG. 12 to match the corresponding experimental scans shown in FIG. 8. A set of parameters that produces the closest match between the theory and experiment defines the solution to the inverse problem, e.g., the depth profile.

As noted above, there are many approaches to solving the inverse problem. One of the more common approaches is to use a least square fitting routine which supplies an initial set of best guesses for the dopant profile to the theoretical model. These best guesses are used to generate a set of theoretical measurement data which is compared to the actual measurement data. To the extent that the values do not match, the theoretical input parameters are adjusted and the theoretical measurement data recalculated using the model and compared to the actual measurement data. This sequence is repeated in iterative fashion until the match between the actual measurements and the calculated measurements falls within a predetermined goodness of fit. Alternatively, the model can be fully parameterized and used to generate a library of theoretical measurement solutions. The actual measurement data can then be compared to the library to find the best match.

Figure 13:
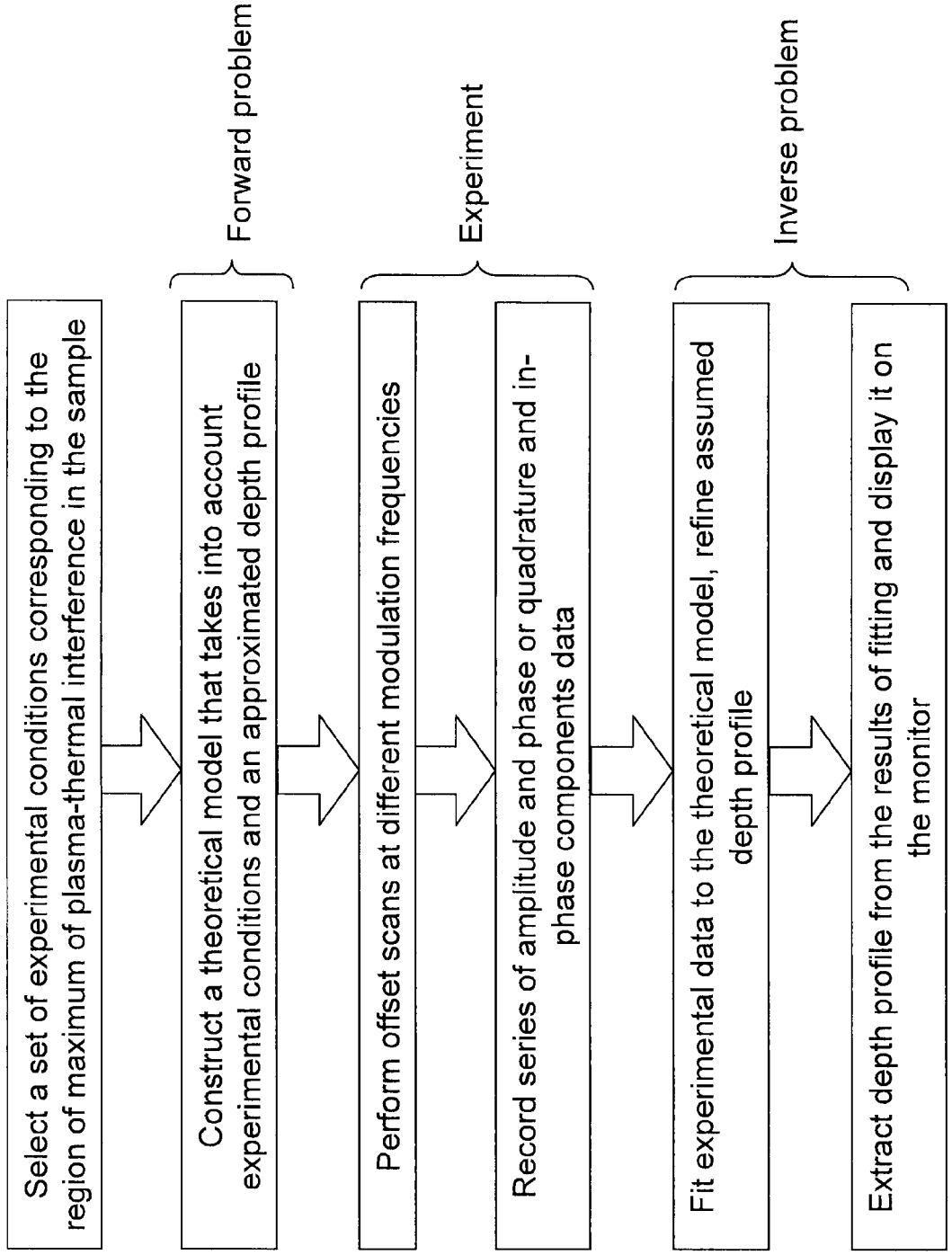
FIG. 13 is a flow chart illustrating one preferred set of steps that can be taken to carry out one aspect of the subject invention.

FIG. 13 illustrates the steps to be followed in this depth profiling method. In a first step, we can select a set of apparatus parameters (wavelength, modulation frequency) which corresponds to the region of maximum plasma-thermal interference. Alternatively, it may be desirable to set up the apparatus parameters to create an MOR signal that is dominated by either thermal or plasma effects.

In a second step, a theoretical model is created that takes into account the experimental conditions and some best guesses of the expected depth profile. Actual measurements are then taken with an apparatus of the type shown in FIG. 3. Typically, the measurements are taken after the initial modeling step, but can be taken in advance and stored for later analysis. The measurements can be taken at different lateral offsets between the pump and probe beams. Also, measurements can be taken at different pump beam modulation frequencies and/or different pump and probe beam wavelengths.

The last two steps of FIG. 13 reflect the solution of the inverse problem wherein the actual measured data (experimental data) is fitted to the theoretical results predicted by the model. Using an iterative analysis, the depth profile can be extracted. This resulting depth profile may be displayed on the screen of a metrology system and/or stored in memory for further analysis and comparison.

As noted above, in addition to lateral offset scans, dopant depth profiling can also be performed by measuring the spectral response of the MOR signal. In a preferred embodiment, the probe beam wavelength is scanned over a predetermined range of wavelengths and the resulting spectral response is fitted to the corresponding theoretical model. As described in U.S. Pat. No. 7,280,215, assigned to the assignee of the current invention and incorporated herein by reference, in certain experimental situations, varying the probe beam wavelength in MOR measurements results in a change of the basic physical mechanism driving the MOR signal. As described in this patent, increasing the probe beam wavelength with a fixed pump wavelength will cause a change in the dominating mechanism from thermal to plasma-wave driven. A thermal-driven MOR signal is more sensitive to thermal properties of the sample such as damage and damage depth profile while a plasma-driven MOR signal is more suitable for carrier depth profiling. Therefore, by selecting an appropriate combination of wavelengths and measuring the MOR signal spectral dependencies, a selective damage or carrier concentration depth profiles can be obtained.

Figure 14:
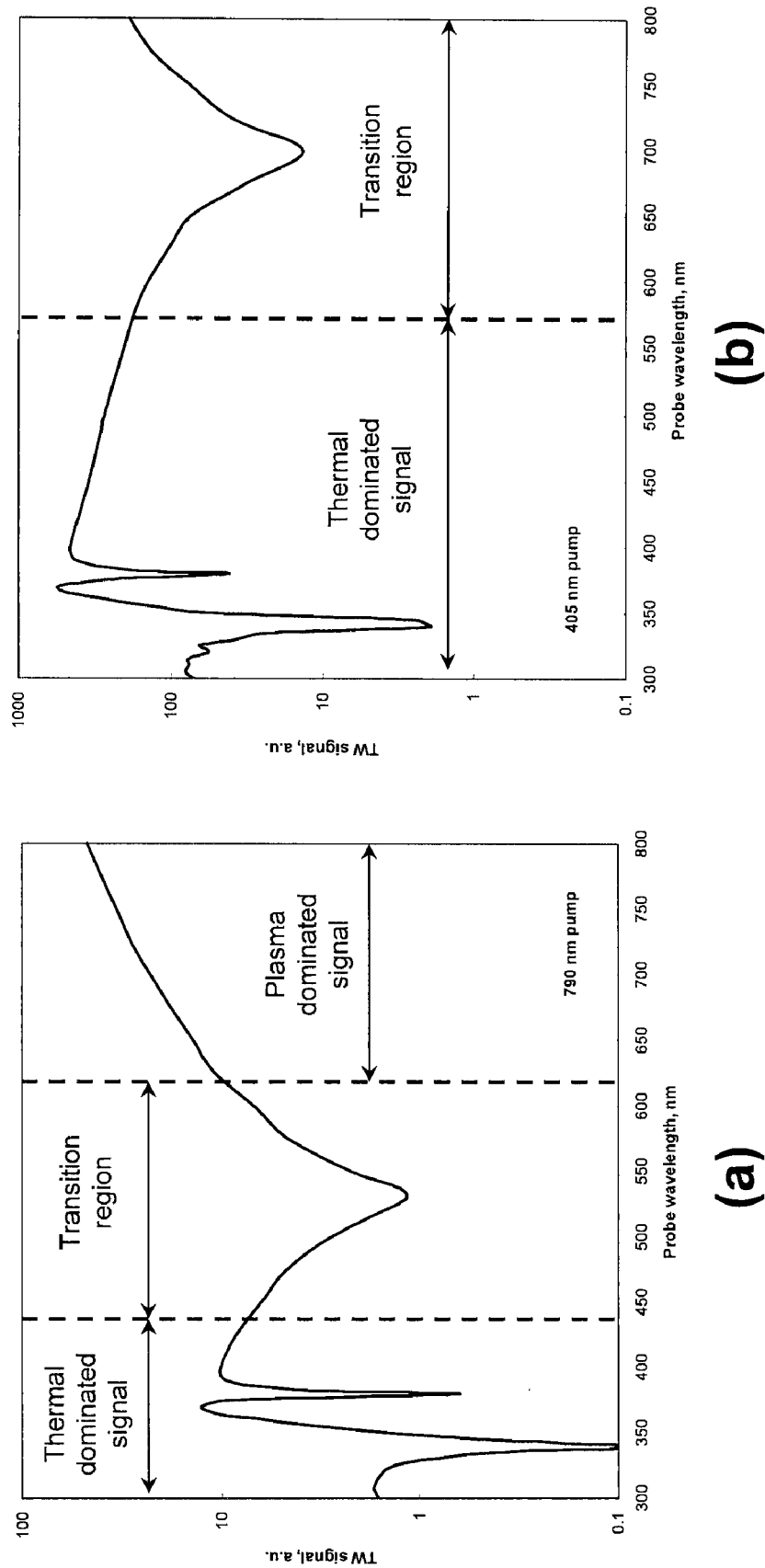
FIGS. 14a and 14b are graphs that illustrate variations in the thermal and plasma contributions to the MOR signals as a function of the probe beam wavelength for two different pump beam wavelengths.

FIG. 14 schematically illustrates the selection of wavelengths for damage depth profiling and carrier depth profiling. For a relatively long pump wavelength of 790 nm (FIG. 14a), probe beam wavelengths below 450 nm can be used for damage depth profiling (thermal dominated MOR signal) while probe beam wavelengths longer than 625 nm are suitable for carrier depth profiling (plasma-dominated MOR signal). For a relatively short pump wavelength of 405 nm (FIG. 14b), probe wavelengths below 575 nm are suitable for damage depth profiling and effective carrier depth profiling can only be performed with probe wavelengths in the IR range (not shown in FIG. 14b).

Tailoring the wavelengths of the pump and probe beams to produce either a plasma or thermally dominated MOR signal is an approach which can also be used in the first embodiment of the subject invention where reconstruction of the depth profile is achieved without using a modeling approach.

In general, increasing the number and variety of measurements that are taken will increase the accuracy of the final result. Depending upon the type of sample and the characteristics to be measured, certain types of measurement variables will provide more useful information. For example, in some cases, measurements at different lateral offsets will be more useful while in others, measurements at different wavelengths will be more useful. In some case, it may be desirable to vary both the offset and wavelength (and/or pump beam modulation frequency). The additional measurement data while useful must be balanced against the increased time that is necessary to obtain the measurements along with greater complexity in the modeling and calculations.

While the subject invention has been described with reference to various preferred embodiments, various changes and modifications could be made therein, by one skilled in the art, without varying from the scope and spirit of the subject invention as defined by the appended claims.

We claim:

1. A method for generating a profile of the carrier concentration in a semiconductor wafer as a function of depth comprising the steps of:

measuring the modulated optical reflectivity of a test wafer and generating output signals in response thereto, said measurements being obtained by periodically exciting the wafer with an intensity modulated pump beam having an energy and modulation frequency sufficient to create thermal and plasma waves that effect the reflectivity of the wafer and monitoring the modulated optical reflectivity changes with a separate probe beam, said measurements being obtained for at least two different separations between the pump and probe beam spots on the wafer;

creating a theoretical model of the wafer;

calculating an optical response of the model using an initial set of parameters and comparing the calculated optical response to the generated output signals and iterating the parameters of the model until the differences between the calculated optical response and the output signals is minimized;

determining a carrier concentration depth profile based on the results of the iteration; and displaying or storing the depth profile.

2. A method as recited in claim 1, wherein the measuring step is performed before the wafer is annealed.

3. A method as recited in claim 1, wherein the measuring step is performed after the wafer is annealed.

4. A method as recited in claim 1, wherein the depth profile is of the active carrier concentration.

5. A method as recited in claim 1, wherein the modulated optical reflectivity measurements are obtained under conditions corresponding to a region of maximum interference between the plasma and thermal waves.

6. A method as recited in claim 1, wherein the modulated optical reflectivity measurements are obtained under conditions corresponding to a region wherein the output signals are primarily plasma driven.

7. A method as recited in claim 1, wherein the modulated optical reflectivity measurements are obtained under conditions corresponding to a region wherein the output signals are primarily thermally driven.

8. A method as recited in claim 1, further including the step of obtaining additional measurements at different probe beam wavelengths and using the measurements to determine the parameter depth profile.

9. A method as recited in claim 1, further including the step of obtaining additional measurements at different pump beam modulation frequencies and using the measurements to determine the parameter depth profile.

10. A method for generating a profile of the index of refraction of a semiconductor wafer as a function of depth comprising the steps of:

measuring the modulated optical reflectivity of a test wafer and generating output signals in response thereto, said measurements being obtained by periodically exciting the wafer with an intensity modulated pump beam having an energy and modulation frequency sufficient to create thermal and plasma waves that effect the reflectivity of the wafer and monitoring the modulated optical reflectivity changes with a separate probe beam, said measurements being obtained for at least two different separations between the pump and probe beam spots on the wafer;

creating a theoretical model of the wafer;

calculating an optical response of the model using an initial set of parameters and comparing the calculated optical response to the generated output signals and iterating the parameters of the model until the differences between the calculated optical response and the output signals is minimized;

determining a depth profile of the index of refraction based on the results of the iteration; and displaying or storing the depth profile.

11. A method for generating a profile of the damage within a semiconductor wafer as a function of depth comprising the steps of:

measuring the modulated optical reflectivity of a test wafer and generating output signals in response thereto, said measurements being obtained by periodically exciting the wafer with an intensity modulated pump beam having an energy and modulation frequency sufficient to create thermal and plasma waves that effect the reflectivity of the wafer and monitoring the modulated optical reflectivity changes with a separate probe beam, said measurements being obtained for at least two different separations between the pump and probe beam spots on the wafer;

creating a theoretical model of the wafer;

calculating an optical response of the model using an initial set of parameters and comparing the calculated optical response to the generated output signals and iterating the parameters of the model until the differences between the calculated optical response and the output signals is minimized;

determining a damage depth profile based on the results of the iteration; and displaying or storing the depth profile.

12. A method for generating a depth profile of a characteristic of a semiconductor wafer comprising the steps of:

measuring the modulated optical reflectivity of a test wafer and generating output signals in response thereto, said measurements being obtained by periodically exciting the wafer with an intensity modulated pump beam having an energy and modulation frequency sufficient to create thermal and plasma waves that effect the reflectivity of the wafer and monitoring the modulated optical reflectivity changes with a separate probe beam, said measurements being obtained for at least two different separations between the pump and probe beam spots on the wafer;

creating a theoretical model of the wafer;

calculating an optical response of the model using an initial set of parameters and comparing the calculated optical response to the generated output signals and iterating the parameters of the model until the differences between the calculated optical response and the output signals is minimized;

determining a depth profile of a characteristic of the wafer based on the results of the iteration, said characteristic being selected from one or more of the group consisting of dopant concentration and defect concentration; and displaying or storing the depth profile.

13. A method as recited in claim 11, wherein the characteristic is dopant concentration.

14. A method as recited in claim 11, wherein the characteristic is defect concentration.

15. A method as recited in claim 11, wherein the measuring step is performed before the wafer is annealed.

16. A method as recited in claim 11, wherein the measuring step is performed after the wafer is annealed.

* * * * *

Disclaimer

7,982,867 B2 — Alex Salnik, Castro Valley, CA (US); Jon Opsal, Livermore, CA (US); Lena Nicolaides, Castro Valley, CA (US). METHODS FOR DEPTH PROFILING IN SEMICONDUCTORS USING MODULATED OPTICAL REFLECTANCE TECHNOLOGY. Patent dated July 19, 2011. Disclaimer filed March 1, 2011, by the assignee, KLA-Tencor Corporation.

The term of this patent shall not extend beyond the expiration date of Pat. No. 7,705,977.

*(Official Gazette September 6, 2011)*